United States Patent [19]
Bezicot

[11] Patent Number: 5,487,382
[45] Date of Patent: Jan. 30, 1996

[54] TRACHEOTOMY FILTER FOR TRACHEOTOMY PATIENTS

[76] Inventor: Robert Bezicot, 48 rue Joseph Fouriaux, 92160 Antony, France

[21] Appl. No.: 232,123
[22] PCT Filed: Oct. 26, 1992
[86] PCT No.: PCT/FR92/00999
  § 371 Date: Apr. 28, 1994
  § 102(e) Date: Apr. 28, 1994
[87] PCT Pub. No.: WO93/08860
  PCT Pub. Date: May 13, 1993

[30] Foreign Application Priority Data
Oct. 30, 1991 [FR] France .................... 91 13378

[51] Int. Cl.⁶ ............................................. A61M 16/00
[52] U.S. Cl. ............................. 128/207.14; 128/207.16
[58] Field of Search .................... 128/200.26, 207.14, 128/207.15, 207.16, 207.29; 623/9

[56] References Cited

U.S. PATENT DOCUMENTS

| | | | |
|---|---|---|---|
| 3,952,335 | 4/1976 | Sorce et al. | 623/9 |
| 4,040,428 | 8/1977 | Clifford | 623/9 |
| 4,325,366 | 4/1982 | Tabor | 128/207.16 |
| 4,538,607 | 9/1985 | Saul | 623/9 |
| 4,582,058 | 4/1986 | Depel et al. | 623/9 |
| 4,759,356 | 7/1988 | Muir | 128/207.16 |
| 4,809,693 | 3/1989 | Rangoni et al. | 128/207.16 |
| 4,994,117 | 2/1991 | Fehder | 128/207.14 |

*Primary Examiner*—Aaron J. Lewis
*Attorney, Agent, or Firm*—Young & Thompson

[57] ABSTRACT

An artificial nose (1) comprising a housing (20) mounted around the surgical opening (3) by a base ring (10) with a two-sided adhesive (15) containing a hydrophilic filtering disc (40) which forms an alternate heat and moisture exchanger between the exhaled and inhaled air. A grid (30) is arranged between the filter (40) and the surgical opening (3) and has a plane front surface (32) contacting the filter, and a convex rear surface (31) with calibrated through-passages. The distance between the front surface (32) and the rear surface (31) ensures, together with the calibre of the through-passages, that mucus ejected from the trachea is essentially unable to reach the filter.

22 Claims, 1 Drawing Sheet

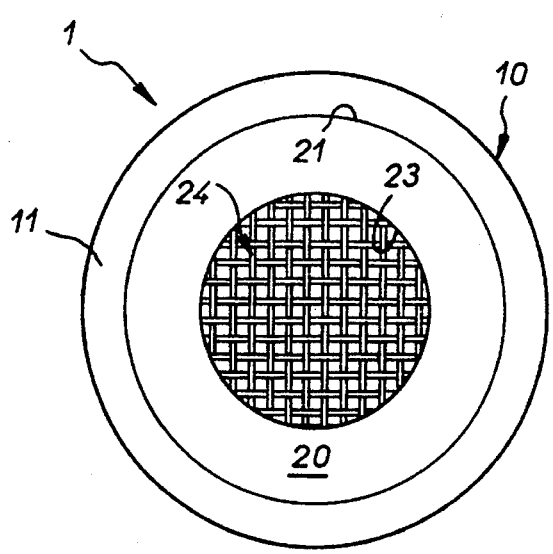
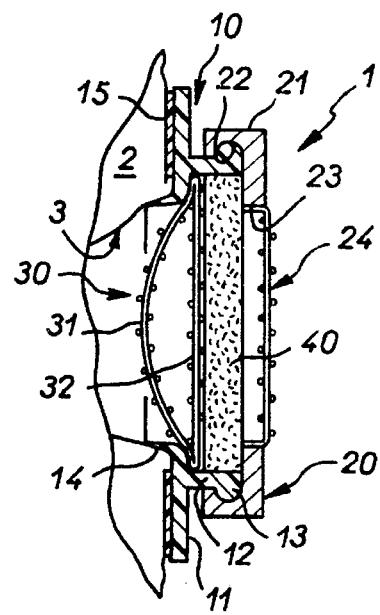
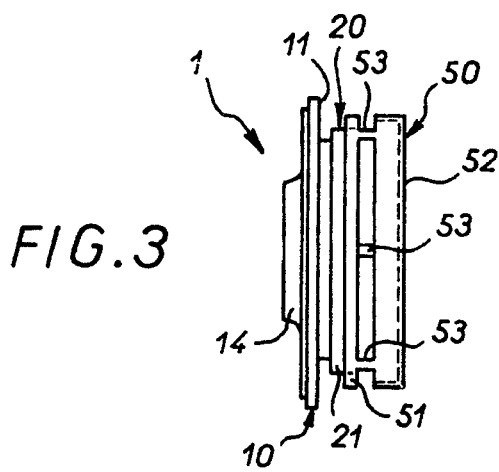
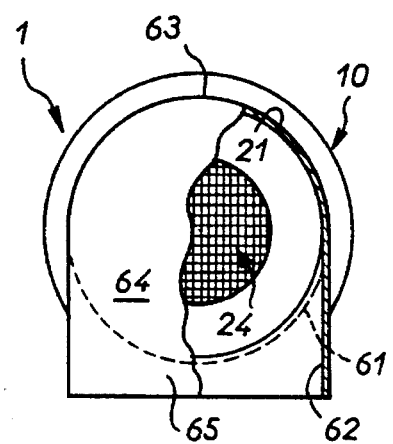
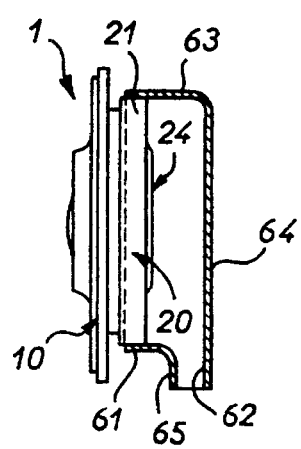
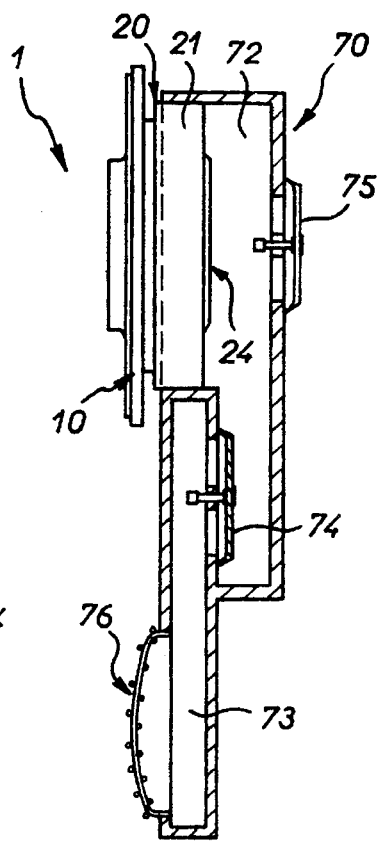

TRACHEOTOMY FILTER FOR TRACHEOTOMY PATIENTS

FIELD OF THE INVENTION

The invention concerns a tracheotomy filter for tracheotomy patients having a surgically formed opening linking the trachea to the skin comprising an apertured casing fastened to the periphery of the surgical opening by an annular flange adhering to the skin, a hydrophilic filter mass forming an exchanger for alternate exchange of heat and moisture between exhaled air and inhaled air and a grill between the filter mass and the surgical opening.

BACKGROUND OF THE INVENTION

In tracheotomy patients, because inhaled air enters the trachea directly it is very important for health reasons and for the patient to be able to breath comfortably that the inhaled air is at substantially the same temperature and contains the same quantities of moisture and dust as if it had reached the trachea after passing through the upper airway (nostrils, nose, pharynx and larynx), meaning a temperature approaching 32° C. with a moisture content approaching saturation at the temperature of this air and substantially free of dust.

The arrangements stated hereinabove enable this result to be achieved to some degree; the filter mass blocks a major part of the dust in suspension in the air, of course; the water vapor contained in the exhaled air, which is saturated at the temperature of the organism, condenses on the filter mass which is therefore heated substantially to the body temperature; inhaled air, arriving at the temperature of the ambient air, is warmed and takes up moisture in contact with the filter mass which is at a higher temperature and contains the condensed water.

However, these known arrangements do not provide sufficient protection against clogging of the pores of the filter mass by mucus expelled from the trachea. A defense measure of the organism against foreign bodies such as dust, microorganisms and dead cells, mucus must be blocked by the grill disposed between the surgical opening and the filter mass; however the current of exhaled air tends to entrain the mucus from the posterior side of the grill on which it is deposited towards the anterior side and from there to spread it over the surface of the filter mass in contact with the anterior side of the grill. Subsequent drying of the mucus forms a hardened crust which clogs the filter mass. The tracheotomy filter must then be replaced.

SUMMARY OF THE INVENTION

An essential objective of the invention is to provide an improved tracheotomy filter whereby clogging of the filter mass is strongly retarded or even prevented.

To this end, the invention proposes a tracheotomy filter for a tracheotomy patient having a surgical opening joining the trachea to the skin comprising in an apertured casing attached to the periphery of the surgical opening by an annular flange adhering to the skin a hydrophilic filter mass forming an exchanger for alternate exchange of heat and moisture between exhaled air and inhaled air and a grill between the filter mass and the surgical opening, characterized in that, the grill being disposed in the casing with spaced apart anterior and posterior components respectively facing the filter mass and the surgical opening, the posterior component has calibrated openings and is spaced from the anterior component by a distance such that, in conjunction with the size of the passages, mucus expelled from the trachea can for the most part not reach the filter mass.

The applicant has found that the rheological properties (viscosity and surface tension) of mucus are such that, after adhering to a grill of appropriate mesh size to block it, it is likely to be drawn out in the direction of the exhaled air current without being detached or breaking and over a significant length dependent on the mesh size of the grill; consequently, by using a grill comprising two components an anterior component in contact with the filter mass and a posterior component exposed to the impact of mucus expelled from the trachea and by separating these grills by a distance greater than the maximum length to which the mucus can be drawn out the mucus blocked by the exterior component is prevented from reaching the filter mass and clogging it.

The filter mass is preferably made from open pore polyurethane foam which combines appropriate hydrophilic properties with appropriate ease of shaping and durability, modest cost and beneficial cleaning possibilities.

The flange preferably comprises a flexible flange surrounding an anterior annular rim over which a complementary bore of the casing fits. This arrangement provides easy access to the filter mass and the grill to replace the former and clean the latter after detaching the tracheotomy filter from the edge of the surgical opening.

The peripheral rim of the flange may comprise a peripheral ring which fits into a complementary groove in the bore of the casing.

To ensure that the tracheotomy filter lines up with the surgical opening it is preferable for the flange to comprise a posterior sleeve aligned with the annular rim and adapted to be inserted into the surgical opening. This achieves exact centring of the bore in the casing with respect to the surgical opening whilst protecting the wall of this opening from unwanted contact with the posterior component of the grill.

In a preferred arrangement the flange is covered with a double-sided adhesive tape which can be renewed to fix the flange effectively to the skin without it being necessary to replace the flange in its entirety.

The anterior component of the grill is preferably flat and its posterior shape is preferably that of a convex dome with a square mesh grill. This shape enables easy and rugged fabrication.

The annular casing with a grill on its anterior side preferably comprises a cap covering the anterior side, parallel to and spaced from the latter, with lateral openings.

The casing in itself is therefore of simple shape and easy to clean and its anterior grill provides an air entry surface area that is relatively large, in particular enabling medication aerosols to be sprayed through it. The cap covers this anterior grill, however, which among other things prevents a high collar blocking the grill.

The cap may comprise a lateral edge which extends to the anterior side over a half-circumference, the other half-circumference opening into an orientable flat skirt. By orienting the skirt vertically downwards, the patient can take a shower without the anterior side of the casing becoming wet, the cover performing the same function as an umbrella.

The cover may also comprise, capping the casing around the anterior side, a valve chamber with an inhalation valve between the chamber and a pipe adapted to be held against the thorax of the patient so as to be substantially at the body temperature and an exhalation valve opening directly to the exterior.

This achieves extremely effective heating of the inhaled air without the extension to the inhaled air path being occupied by exhaled air containing carbon dioxide and other exhaled gaseous pollutants.

BRIEF DESCRIPTION OF THE DRAWINGS

Secondary features and advantages of the invention will emerge from the following description given by way of example with reference to the appended drawings in which:

FIG. 1 is a side view in cross-section of a tracheotomy filter in accordance with the invention;

FIG. 2 is a front view of a tracheotomy filter fitted with a go-anywhere cap;

FIG. 3 is a side view of a tracheotomy filter fitted with a go-anywhere cap;

FIGS. 4A and 4B are respectively front and side views of a tracheotomy filter fitted with a cap protecting against running liquid;

FIG. 5 is a view in transverse cross-section of a tracheotomy filter fitted with a cap designed to improve the warming of inhaled air.

DETAILED DESCRIPTION OF THE INVENTION

In the selected embodiment shown in FIGS. 1 and 2 the tracheotomy filter 1 comprises a circular elastomer flange 10 and a rigid metal or molded polymer casing 20. The flange 10 comprises an annular flange 11 around an annular rim 12. Using double-sided adhesive tape 15 which provides a fluid-tight join, the flange 11 is fixed to the skin at the base of the neck 2 of a tracheotomy patient around a surgical opening 13 which joins the trachea to the skin. A sleeve 14 more or less aligned with the rim 12 projects around the central apperture in the flange 11 and is inserted in the surgical opening 3 to centre the tracheotomy filter 1 relative to the surgical opening.

Taking the tracheotomy patient as the orientation reference point, the rim 12 occupies an anterior position and the sleeve 14 a posterior position relative to the flange 11. In what follows these terms "anterior" and "posterior" will be used in relation to the patient wearing the tracheotomy filter.

The rim 12 is a section of tube; at its anterior end it is fitted with a ring 13 projecting from the periphery of the tube section.

The generally disk-shaped casing 20 includes a tubular rim 21 in the bore of which is formed a groove 22 complementary to the ring 13 whereby the casing 20 is removably fixed to the flange 10. The anterior side of the casing 20 includes a circular window 23 aligned with the central aperture in the flange 10 and provided with a grill 24.

The casing 20 houses a disk-shaped filter mass 40 which is made from an open pore polyurethane foam with hydrophilic properties.

A barrier grill 30 is disposed between the filter mass 40 and the surgical opening 3. The grill 30 has a convex posterior component 31 and a plane anterior component 32. These component are joined by their circular edges in a ring which abuts the anterior periphery of the central opening in the flange 10. The convex posterior component 31 and in this embodiment the anterior component 32 are in the form of a grill with a square mesh of approximately 4 mm.

Apart from the fact that it facilitates centring of the tracheotomy filter in the surgical opening, the sleeve 14 prevents the posterior component 31 of the grill 30 bearing directly against the edge of the surgical opening 3, despite the fact that by virtue of its convex shape it enters this opening.

In the known manner, the filter disk 40 is cooled by the ambient air and causes some of the moisture contained in the exhaled air to condense, the moisture content of the exhaled air being the saturation moisture content at the temperature of the lungs. Most of the condensed moisture remains in the filter mass, because of its hydrophilic properties. The condensation warms the filter mass by releasing the latent heat of evaporation. During the next indrawn breath, the inhaled air takes up moisture by evaporation of some of the moisture retained by the filter mass and is warmed through contact with the moisture that is not taken up. After a few respiratory cycles (exhalation and inhalation) steady state conditions are obtained similar to those which apply in the case of natural respiration through the upper airway.

The function of the blocking grill is to block mucus expelled from the trachea. The mucus, formed by organic defense reaction against attack by dust, microorganisms and detached dead cells in particular, is in the form of an aqueous gel often of high viscosity and with sufficient surface tension to form autonomous globules.

If the mucus reaches the moist filter mass 40 it tends to spread thereon and then to dry in contact with the inhaled air as this takes up the water constituting the gel. This clogs the filter mass.

However, the relatively large pieces of mucus which would cause most of the clogging of the filter mass strike the convex posterior component 31 of the grill 30 and stick to it. Their viscosity and surface tension prevent them being fragmented by entrainment in the exhaled air with the result that they are drawn out in the direction of this air current in the space between the posterior component 31 and the anterior component 32, but without reaching the filter mass 40, whilst continuing to adhere to the posterior component of the grill.

It will be understood that if the mesh size of the posterior component 31 of the grill 30 is too small the mucus will clog the grill. If the mesh size is too large, on the other hand, the probability that the posterior side 31 of the grill 30 will block the mucus becomes low and the grill becomes less effective. Experiments have shown that a 4 mm square mesh with a wire diameter of around 1 mm works well.

It will have been understood that the plane anterior side 32 of the grill 30 serves only to hold the filter mass 40 in position so that it is not drawn against the posterior component 31 by the inhaled air.

The presence of the double-sided adhesive tape 15, which is of course of a physiologically acceptable kind, enables re-use of the tracheotomy filter after it has been removed by replacing the ring 15 of double-sided adhesive tape which will have lost its adhesive properties after being detached. The casing is easy to open so that the spent filter mass 40 can be replaced and the grill 30 cleaned.

Note that the relatively large size of the window 23 enables medication aerosols to be sprayed onto the filter mass 40 through the grill 24.

In everyday life, however, the fact that the window 23 is open at the front has the drawback of being exposed to direct contact, especially with the clothes, and is not particularly esthetic.

FIG. 3 shown to a smaller scale a tracheotomy filter 1 which is fitted with a cap 50 primarily to prevent the wearer's clothes blocking the window 23 in the cover 20. The cap 50 comprises a ring 51 which slides with moderate friction on the rim 21 of the casing 20, a front plate 52 the same outside diameter as the ring 51 and spacers 53 between the ring and the front plate 52. In addition to its function of protecting the window 23 of the casing, the cap 50 conceals the opening and the grill and can be finished in a way which softens the functional appearance of the casing.

The cap 50 as shown in FIG. 3 can additionally be used by persons who wear an implant to re-enable speaking through the mouth, the operation of this implant requiring temporary blocking of the surgical opening. To this end the sliding travel of the ring 51 over the periphery or edge 21 of the casing 20 is sufficient to allow the front plate 52, which is normally spaced from the window 23, to be pressed in until it contacts the anterior side of the casing and blocks the window 23.

FIGS. 4A and 4B show a cap specifically designed to protect the tracheotomy filter 1 from running liquid, during a shower or while participating in water sports, for example. A circular ring 61 on the cap 60 fits over the peripheral edge 21 of the casing of the tracheotomy filter 1 with moderate friction. Over one half-circumference the ring 61 is extended by an edge 63 which extends as far as a front plate 64. Over the other half-circumference the ring 61 is joined to a plate 65 parallel to the front plate 64. The plates 64 and 65 are joined together at the sides to form conjointly a flat skirt 62.

It will be understood that by directing the opening in the flat skirt 62 downwards the tracheotomy filter 1 is protected umbrella-fashion so that a shower can be taken with no risk of drowning.

The cap shown in FIG. 5 has been designed with the intention of improving the heating of inhaled air, especially in cold weather. This cap 70 comprises two oblong chambers, one chamber 72 which has an annular edge 71 which fits with moderate friction over the peripheral edge 21 of the cover of the tracheotomy filter 1 and another chamber 73 below the ring 71, the chambers 72 and 73 having a common wall to enable partial overlapping of the chambers. The chamber 72 has a valve 75 facing the grill 24 of the cover of the tracheotomy filter adapted to open from the inside towards the outside in response to the increase in pressure on exhalation and a valve 74 closing an opening in the wall common to the chambers 72 and 73 and adapted to open from the chamber 73 into the chamber 72 in response to a reduction in pressure in the chamber 72 on inhalation.

The chamber 73 has a ducting function and includes in its lower part and in the wall facing towards the body of the patient a window protected by a convex grill 76 which bears against the thorax of the patient below the surgical opening.

The inhaled air will therefore be taken from below the clothing, in contact with the thorax, through the chamber 73 whose walls are also substantially at body temperature and then, after passing through the valve 74, through the chamber 72 before reaching the tracheotomy filter 1. Exhaled air, on the other hand, passes directly from the chamber 72 to the exterior through the valve 75. This prevents the formation of a dead volume of expired vitiated air containing a high percentage of carbon dioxide in the passageway 73 conveying air warmed by contact with the body.

The invention is of course not limited to the examples described but encompasses all variant executions thereof within the scope of the claims.

Note that the arrangement of FIG. 5 could be adapted to breathing from an air supply via a breathable air pipe, for example for scuba diving or snorkelling.

I claim:

1. Tracheotomy filter for a tracheotomy patient having a surgical opening joining the trachea to the skin, said tracheotomy filter comprising an apertured casing having an annular flange for attaching the casing to a peripheral skin zone surrounding the surgical opening, the apertured casing housing a hydrophilic filter mass forming an exchanger for alternate exchange of heat and moisture between exhaled air and inhaled air and a grill disposed to one side of the filter mass facing the surgical opening, the grill comprising anterior and posterior grill components respectively facing the filter mass and the surgical opening, a space being defined between operative central portions of said anterior and posterior components, said posterior component having openings defined for blocking penetration of mucus and said filter mass being sufficiently spaced from said posterior component whereby most mucus expelled from the trachea is prevented from reaching the filter mass.

2. Tracheotomy filter according to claim 1, wherein the filter mass comprises open pore polyurethane foam.

3. Tracheotomy filter according to claim 1, wherein the flange comprises a flexible flange extending around an anterior annular member, a complementary annulus being releasably cooperable with the annular member.

4. Tracheotomy filter according to claim 3, wherein a bead is provided on one of the annular member and annulus engageable with a groove defined on the other of the annular member and annulus.

5. Tracheotomy filter according to claim 3, wherein the flange further comprises a posterior sleeve aligned with the anterior annular member and adapted to be received in the surgical opening.

6. Tracheotomy filter according to claim 1, further comprising a strip of double-sided adhesive tape adapted to overlie the flange and to be applied to the skin.

7. Tracheotomy filter according to claim 1, wherein the anterior component of the grill is planar and its posterior component is a convex dome and defined by square mesh.

8. Tracheotomy filter according to claim 1, wherein the casing is annular, a grill being fitted at an anterior end of the casing.

9. Tracheotomy filter according to claim 8, further comprising, capped on the anterior end of the casing, a valve chamber with an inhalation valve between the chamber and a pipe adapted to be applied against the thorax of the patient so as to be substantially at body temperature and an exhalation valve opening directly to the exterior.

10. Tracheotomy filter according to claim 8, further comprising a cap fitted on the anterior end of the casing and parallel to and spaced therefrom, the cap having lateral openings.

11. Tracheotomy filter according to claim 10, wherein the cap comprises a front plate and a ring spaced therefrom, the ring being snugly received on the periphery of the casing for limited travel sufficient to enable the front plate to close off the anterior end of the casing.

12. Tracheotomy filter according to claim 10, wherein the cap has a lateral edge which extends substantially halfway around the circumference of the anterior end of the casing, a remaining portion of the circumference opening into an orientable flat skirt.

13. Tracheotomy filter according to claim 1, further comprising means for removably mounting said grill independently of said apertured casing to facilitate cleaning of the grill.

14. Tracheotomy filter for a tracheotomy patient having a surgical opening joining the trachea to the skin, said tracheotomy filter comprising an apertured casing having an annular flange for attaching the casing to a peripheral skin zone surrounding the surgical opening, the apertured casing housing a hydrophilic filter mass forming an exchanger for alternate exchange of heat and moisture between exhaled air and inhaled air and a grill disposed to one side of the filter mass facing the surgical opening, the grill having spaced anterior and posterior components respectively facing the filter mass and the surgical opening, said posterior component having openings defined for blocking penetration of mucus and said filter mass being sufficiently spaced from said posterior component whereby most mucus expelled from the trachea is prevented from reaching the filter mass, and means for removably mounting said grill in said apertured casing to facilitate cleaning of the grill.

15. Tracheotomy filter according to claim 14, wherein posterior component of the grill extends posteriorly relative to the apertured casing.

16. Tracheotomy filter according to claim 14, wherein said anterior component of the grill is immediately proximate said filter mass.

17. Tracheotomy filter according to claim 14, wherein said annular flange extends radially inwardly beyond the outer peripheral edge of the grill to remain said grill against posterior movement.

18. Tracheotomy filter according to claim 14, further comprising a removable annulus cooperable with an anterior end of the apertured casing for retaining the filter anteriorly.

19. Tracheotomy filter according to claim 14, wherein outer peripheral edges of said grill and filter mass are sandwiched between a radially inwardly extending portion of the annular flange and a radially inwardly extending portion of an annulus removably mounted on an anterior end of said annular casing.

20. Tracheotomy filter according to claim 14, wherein said posterior component is posteriorly convex.

21. Tracheotomy filter according to claim 20, wherein said anterior and posterior components of the grill are joined to each other at outer peripheral edges thereof.

22. Tracheotomy filter according to claim 14, wherein the grill components comprise a square mesh of about 4 mm.

* * * * *